(12) United States Patent
Higgins (10) Patent No.: US 6,660,250 B1
(45) Date of Patent: Dec. 9, 2003

(54) TOOTH CLEANING COMPOSITION AND APPLICATOR

(76) Inventor: Pete B Higgins, 4001 Geist Rd., Suite 3, Fairbanks, AK (US) 99709

( * ) Notice: Subject to any disclaimer, the term of this patent is extended or adjusted under 35 U.S.C. 154(b) by 0 days.

(21) Appl. No.: 10/233,446

(22) Filed: Sep. 3, 2002

(51) Int. Cl.$^7$ .................. A61K 7/16; A61C 15/00
(52) U.S. Cl. .................. 424/49; 51/307; 433/215; 433/216
(58) Field of Search ............ 424/49–58; 51/307; 433/215, 216

(56) References Cited

U.S. PATENT DOCUMENTS

| | | | | |
|---|---|---|---|---|
| 3,228,845 A | * | 1/1966 | Najjar | 167/93 |
| 3,718,973 A | * | 3/1973 | Slater et al. | 32/22 |
| 3,935,306 A | | 1/1976 | Roberts | |
| 4,089,943 A | | 5/1978 | Roberts | |
| 4,143,126 A | * | 3/1979 | Gaffar | 424/67 |
| 4,165,366 A | * | 8/1979 | Mellberg | 424/49 |
| 4,165,368 A | * | 8/1979 | Gaffar | 424/49 |
| 4,486,175 A | | 12/1984 | Fisher et al. | |
| 4,604,058 A | | 8/1986 | Fisher et al. | |
| 4,669,492 A | | 6/1987 | von Kleinsorgen | |
| 5,178,538 A | | 1/1993 | Eckert | |
| 5,334,020 A | | 8/1994 | Eckert | |
| 5,660,546 A | * | 8/1997 | Shafer | 433/216 |
| 5,698,182 A | | 12/1997 | Prencipe et al. | |
| 5,967,154 A | | 10/1999 | Anderson | |
| 6,004,539 A | * | 12/1999 | Longo et al. | 424/49 |
| 6,187,294 B1 | * | 2/2001 | Penner | 424/49 |
| 6,280,707 B1 | * | 8/2001 | Peterson et al. | 424/49 |
| 6,488,913 B2 | * | 12/2002 | Orlowski et al. | 424/53 |

* cited by examiner

*Primary Examiner*—Shep K. Rose
(74) *Attorney, Agent, or Firm*—Michael I Kroll

(57) ABSTRACT

The present invention discloses a tooth cleaning composition and applicator that is particularly adapted for clearing and cleaning the area of the teeth in preparation of fillings or orthodontic appliances, such as braces or bridges. The cleaning agent of the present invention consists of various size ground pumice with a water soluble lubricant binder. The present invention limits the tendencies of spatter and overcomes prior art uses of ground pumice in dental applications.

3 Claims, 10 Drawing Sheets

14

| | PUMICE POWDER PARTICLE SIZE | |
|---|---|---|
| 28 | MEDIUM GRIT PUMICE | (121-160μM) |
| 30 | FINE GRIT PUMICE | (81-120μM) |
| 32 | EXTRA FINE GRIT PUMICE | (41- 80μM) |
| 34 | ULTRA FINE GRIT PUMICE | (0 - 40μM) |

| PUMICE POWDER PARTICLE SIZE | |
|---|---|
| 28 MEDIUM GRIT PUMICE | (121-160µM) |
| 30 FINE GRIT PUMICE | (81-120µM) |
| 32 EXTRA FINE GRIT PUMICE | (41-80µM) |
| 34 ULTRA FINE GRIT PUMICE | (0-40µM) |

TOOTH CLEANING COMPOSITION AND APPLICATOR

FIELD OF THE INVENTION

The present invention relates generally to dental cleaning compositions, more specifically, to dental cleaning composition and employment for the cleaning of an area in preparation of dental applications.

The teeth cleaning element of the present invention is particularly adapted for clearing and cleaning the area of the teeth in preparation of fillings or orthodontic appliances, such as braces or bridges.

The cleaning agent of the present invention consists of pumice power. Pumice is a light-colored, frothy volcanic rock, usually of dacite or rhyolite composition, formed by the expansion of gas in erupting lava. It is well established that ground pumice is an effective matter that is used as an abrasive cleaning agent including dental products.

It is also known that the said ground pumice is subject to splatter and can be difficult to maintain the cleaning agent in a localized area. The present invention limits the tendencies of spatter and overcomes prior art uses of ground pumice.

The composition of the present invention consists of pumice powder and a water-soluble lubricant. Using an equal portion by weight, 1 part pumice powder and 3 part water-soluble lubricant, the two components are mixed into a consistent pumice solution.

The pumice solution is then deposited into a syringe for application. The preferred embodiment of the syringe specifications for applying the pumice solution includes a 20 cc syringe applicator with a #20 tip.

A benefit of the present invention enables the said pumice solution deposited in the syringe to be packaged in a pre-sealed purified container for future use. Such packaging prevents possible contamination and allows for extended shelf life of the pumice solution composition.

Measured in microns, typical pumice power for use in dental applications can vary from 0–160 μm. Another preferred embodiment of the present invention includes greater division of the size of the pumice powder granules.

The present invention sub-divides the 0–160 μm pumice powder range into four sizes. Medium grit ranges from 121–160 μm pumice powder granules. Fine grit ranges from 81–120 μm pumice powder granules. Extra fine grit ranges from 41–80 μm pumice powder granules. Ultra fine grit ranges from 0–40 μm pumice powder granules.

The division of pumice powder granules provides the present invention with four unique compositions to provide the user increased preference or abrasive need requirements.

In addition to the stabilizing benefit of the water soluble lubricant, the lubricant is sterile, greaseless and harmless if ingested. Furthermore, cleanup upon completion of the tooth cleansing is simplified as the composition is liquefied by the saliva.

DESCRIPTION OF THE PRIOR ART

There are other teeth cleaning compositions. Typical of these is U.S. Pat. No. 3,935,306 issued to Francis D. Roberts et al. on Jan. 27, 1976.

Another patent was issued to Francis D. Roberts et al. on May 16, 1978 as U.S. Pat. No. 4,089,943. Yet another U.S. Pat. No. 4,486,175 was issued to Leo Fisher et al. on Dec. 4, 1984 and still yet another was issued on Aug. 5, 1986 to Leo Fisher et al. as U.S. Pat. No. 4,604,058.

Another patent was issued to Reinhard von Kleinsorgen on Jun. 2, 1987 as U.S. Pat. No. 4,669,492. Yet another U.S. Pat. No. 5,178,538 was issued to Ronald C. Eckert on Jan. 12, 1993. Another was issued to Ronald C. Eckert on Aug. 2, 1994 as U.S. Pat. No. 5,334,020 and still yet another was issued on Aug. 26, 1997 to Joseph G. Shafer as U.S. Pat. No. 5,660,546.

Another patent was issued to Michael Prencipe et al. on Dec. 16, 1997 as U.S. Pat. No. 5,698,182. Yet another U.S. Pat. No. 5,967,154 was issued to Michael R. Anderson on Oct. 19, 1999. Another was issued Kenneth S. Peterson et al. on Aug. 28, 2001 as U.S. Pat. No. 6,280,707 and still yet another was issued on Feb. 13, 2001 to Russell Anthony Penner as U.S. Pat. No. 6,187,294.

U.S. Pat. No. 3,935,306

Inventor: Francis D. Roberts et al.

Issued: Jan. 27, 1976

Toothpaste formulations having dispersed therein a plurality of agglomerated particles of dental polishing agent that are visible, palpable and substantially insoluble in the toothpaste are disclosed. The agglomerates comprise individually impalpable particles of water insoluble dental polishing agent; can include an agglomerating agent and are reduced to smaller sized particles of dental polishing agent when subjected to mild mechanical agitation such as toothbrushing. Such agglomerates are particularly well suited for incorporation into transparent gel dental vehicles to provide special effects such as supplemental cleaning and polishing characteristics without adversely affecting the visual clarity of the finished toothpaste.

U.S. Pat. No. 4,089,943

Inventor: Francis D. Roberts et al.

Issued: May 16, 1978

Toothpaste formulations having dispersed therein a plurality of agglomerated particles of dental polishing agent that are visible, palpable and substantially insoluble in the toothpaste are disclosed. The agglomerates comprise individually impalpable particles of water insoluble dental polishing agent; can include an agglomerating agent and are reduced to smaller sized particles of dental polishing agent when subjected to mild mechanical agitation such as toothbrushing. Such agglomerates are particularly well suited for incorporation into transparent gel dental vehicles to provide special effects such as supplemental cleaning and polishing characteristics without adversely affecting the visual clarity of the finished toothpaste.

U.S. Pat. No. 4,486,175

Inventor: Leo Fisher et al.

Issued: Dec. 4, 1984

A dental appliance has an elongated hollow tube within the interior of which is mounted for rotation an elongated drive shaft. One end of the tube is coupled to a handle as is the drive shaft which is driven from the handle in rotation. A head joined to the other end of the tube defines an interior cavity within which a hub is mounted for rotation about an axis disposed at an angle with respect to the drive shaft. Motion is translated from the drive shaft to the hub. An opening in the head enables the hub to be accessed through the opening. Included in the hub is a barrel section for securing a variety of dental attachments thereto. A seal is created between the opening from the cavity and the hub in order to prevent fluid flow therethrough. Lubricant is introduced within the tube and the drive shaft actuates an auger or the equivalent for propelling the lubricant into the motion translator.

U.S. Pat. No. 4,604,058

Inventor: Leo Fisher et al.

Issued: Aug. 5, 1986

A dental appliance has an elongated hollow tube within the interior of which is mounted for rotation an elongated drive shaft. One end of the tube is coupled to a handle as is the drive shaft which is driven from the handle in rotation. A head joined to the other end of the tube defines an interior cavity within which a hub is mounted for rotation about an axis disposed at an angle with respect to the drive shaft. Motion is translated from the drive shaft to the hub. An opening in the head enables the hub to be accessed through the opening. Included in the hub is a barrel section for securing a variety of dental attachments thereto. A seal is created between the opening from the cavity and the hub in order to prevent fluid flow therethrough. Lubricant is introduced within the tube and the drive shaft actuates an auger or the equivalent for propelling the lubricant into the motion translator.

U.S. Pat. No. 4,669,492

Inventor: Reinhard von Kleinsorgen

Issued: Jun. 2, 1987

A cosmetic stick for a powder pencil comprises a stable stick body formed from powder base material and pigment, optionally with binding agent, lubricant and/or adhesion-enhancing agent, together with a particulate material which is additionally contained in the stick body in finely divided form, the particles thereof being harder than the base materials. The particulate material includes at least one derivative of tricalcium phosphate, tetracalcium phosphate or calcium pyrophosphate.

U.S. Pat. No. 5,178,538

Inventor: Ronald C. Eckert

Issued: Jan. 12, 1993

An improved prophylactic cup device comprised of a prophylactic cup mounted on a mounting screw is described. In the preferred embodiment, the prophylactic cup is molded from a silicone polymer containing a dental cleaning and polishing agent such as pumice and is mounted onto a circular cross-sectioned mounting screw comprised of a shaft with a threaded portion and a head. The head provides for cylindrical inlet or channel portions and retaining slots. Since silicone polymers are poorly adherent to any surface and because the strength of silicone polymers is greatly reduced by the addition of pumice, the channels and retaining slots increase the contact surface area between the prophylactic cup and the mounting screw. This allows the prophylactic cup device to be mounted on a dental handpiece and to be used to clean teeth and gingival crevices without a dental paste. A prophylactic cup device and a dental handpiece comprising a disposable unit are also shown.

U.S. Pat. No. 5,334,020

Inventor: Ronald C. Eckert

Issued: Aug. 2, 1994

An improved prophylaxis cup formed of a silicone elastomer incorporated with a pumice material uniformly incorporated throughout the cup and mounted on a mounting button in a non-disposable dental handpiece is described. After a teeth cleaning procedure, the prophylaxis cup is disposed of and the mounting button and the dental handpiece are sterilized for reuse. The mounting button is comprised of a bulbous mounting head having a circular cross-section that mates with a similarly shaped cavity in a mounting section of the cup. The cavity is preferably about 5 to 15 percent smaller in cross-sectional diameter than the mounting head so that the cup must be stretched over the mounted head for mounting the cup on the mounting button. A working section of the cup is provided with a conical recess that wears down as the teeth are being cleaned to provide continuous application of fresh abrasive to the tooth surface. The prophylaxis cup mounted on a disposable dental handpiece or angled attachment is also shown Further, the process for manufacturing the prophylaxis cup is described.

U.S. Pat. No. 5,660,546

Inventor: Joseph G. Shafer

Issued: Aug. 26, 1997

A home denture cleaning kit for cleaning dentures. The kit includes at least a one year's supply of dental pumice, at least a one year supply of tin oxide and an electric driven rotating brush. In a preferred embodiment the bristles of the brush are at least ½ inch long and no longer than about 1¼ inch and are aligned generally parallel to the axis of rotation of the brush. Dentures are cleaned by mixing about one gram of pumice with an equal quantity of water to form a paste which is applied to the dentures. The rotating brush is then used to brush the pumice-water paste against the denture material to remove film and surface stains such as those due to coffee and tea. After the teeth are cleaned, approximately ⅛ gram of tin oxide powder is mixed with an equal quantity of water and applied to the teeth portion of the dentures. The rotating buffing wheel is then used to buff the tin-oxide paste against the dentures in order to produce a shine on the dentures.

U.S. Pat. No. 5,698,182

Inventor: Michael Prencipe et al.

Issued: Dec. 16, 1997

A method for inhibiting dental calculus concomitant with tooth whitening is disclosed wherein there is applied to the teeth an oral composition containing in a vehicle an amount of a anticalculus phosphate salt and an amount of calcium peroxide effective to whiten teeth, the vehicle containing about 4 to about 9% by weight water and an amount of calcined alumina effective to heighten the whitening effect of the $CaO_2$, and allowing the composition to remain on the teeth for a time sufficient to effect whitening thereof.

U.S. Pat. No. 5,967,154

Inventor: Michael R. Anderson

Issued: Oct. 19, 1999

Dental hygiene filament, for use as dental floss or as bristles for a tooth brush for flossing and/or brushing teeth, comprising an elongated body defining an exterior surface having an abrasive, granular substance, such as pumice, uniformly distributed thereon. The granular material is firmly attached to the filament so that, when used as dental floss, pulling on the ends of the floss between the teeth allows for aggressive and efficient removal of plaque while moving the dental floss across the surface, as recommended by dentists. In addition, the irregular surface area acts to cause additional frictional interaction between the filament's granular material and the tooth surface, quickly and efficiently removing the plaque and providing a greater surface area for removing plaque. Each filament embodiment may include a microbicide for preventing bacterial growth.

U.S. Pat. No. 6,280,707

Inventor: Kenneth S. Peterson et al.

Issued: Aug. 28, 2001

An oral prophalaxis paste includes a preselected grade and amount of abrasive material such as pumice clay or diatimoceous earth. The abrasive material is moistened with water and a moisture retention agent such as glycerin is included. A curing system is employed, such as using sodium silicate and methyl salicylate. The formulation provides antimicrobial properties by the inclusion of triclosan.

U.S. Pat. No. 6,187,294

Inventor: Russell Anthony Penner

Issued: Feb. 13, 2001

A topical anesthetic/prophylaxis paste is provided that is effective at removing extrinsic stains and plaque on the teeth and at reducing discomfort during scaling procedures thereon by delivery of an anesthetic into the gingival sulcus. The paste includes at least one topical anesthetic, either 5% Lidocaine or 20% Benzocaine, at least one humectant, preferably a Polyethylene glycol in the amount of about 28 to about 42 percent by weight, at least one abrasive agent, preferably pumice in the amount of about 55 to about 65 percent by weight, and at least one sweetener, preferably Saccharin sodium in the amount up to about three percent by weight. A method of delivering the topical anesthetic/prophylaxis paste into the sulcus by a low speed handpiece with a prophylaxis angle and rubber cup is also provided.

While these dental appliances, equipment, and methods may be suitable for the purposes for which they were designed, they would not be as suitable for the purposes of the present invention, as hereinafter described.

SUMMARY OF THE PRESENT INVENTION

A primary object of the present invention is to provide means for cleaning the area of the tooth or teeth in preparation for dental application.

Another object of the present invention is to provide means for using pumice powder as a cleaning agent in preparation of dental applications.

Another object of the present invention is to provide means for using a water soluble lubricant to formulate a non-splatter pumice solution.

Another object of the present invention is to provide means for applying the pumice solution through a syringe.

Another object of the present invention is to provide means for storing and protecting the pumice solution for future use.

One other object of the present invention is to provide means for using various size pumice powder granules.

Another object of the present invention is to provide means for segregating the pumice power size granules into four standard sizes.

Yet another object of the present invention is to provide an efficient means for preparing teeth for dental applications.

One other object of the present invention is to provide an economical means for preparing teeth for dental applications.

Additional objects of the present invention will appear as the description proceeds.

The present invention overcomes the shortcomings of the prior art by providing means for efficient and effective use of pumice in tooth preparation for dental applications.

To the accomplishment of the above and related objects, this invention may be embodied in the form illustrated in the accompanying drawings, attention being called to the fact, however, that the drawings are illustrative only, and that changes may be made in the specific construction illustrated and described within the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

The following is a list of the reference numerals used in the drawings:
10 tooth cleaning composition and applicator
12 syringe applicator
14 pumice powder
16 water soluble lubricant
18 dentist, (user)
20 patient
22 teeth
24 #20 tip
26 packaging for pumice solution and applicator
28 medium grit pumice
30 fine grit pumice
32 extra fine grit pumice
34 ultra fine grit pumice 36 process for medium grit pumice solution
38 process for fine grit pumice solution
40 process for extra fine grit pumice solution
42 process for ultra fine grit pumice solution
44 canister
46 plunger
48 egress port
50 needle-like conduit The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

DETAILED DESCRIPTION OF THE PREFERRED EMBODIMENTS

The following discussion describes in detail one embodiment of the invention. This discussion should not be construed, however, as limiting the invention to this particular embodiment. Practitioners skilled in the art will recognize numerous other embodiments as well. For a definition of the complete scope of the invention, the reader is directed to the appended claims.

Figure 1:
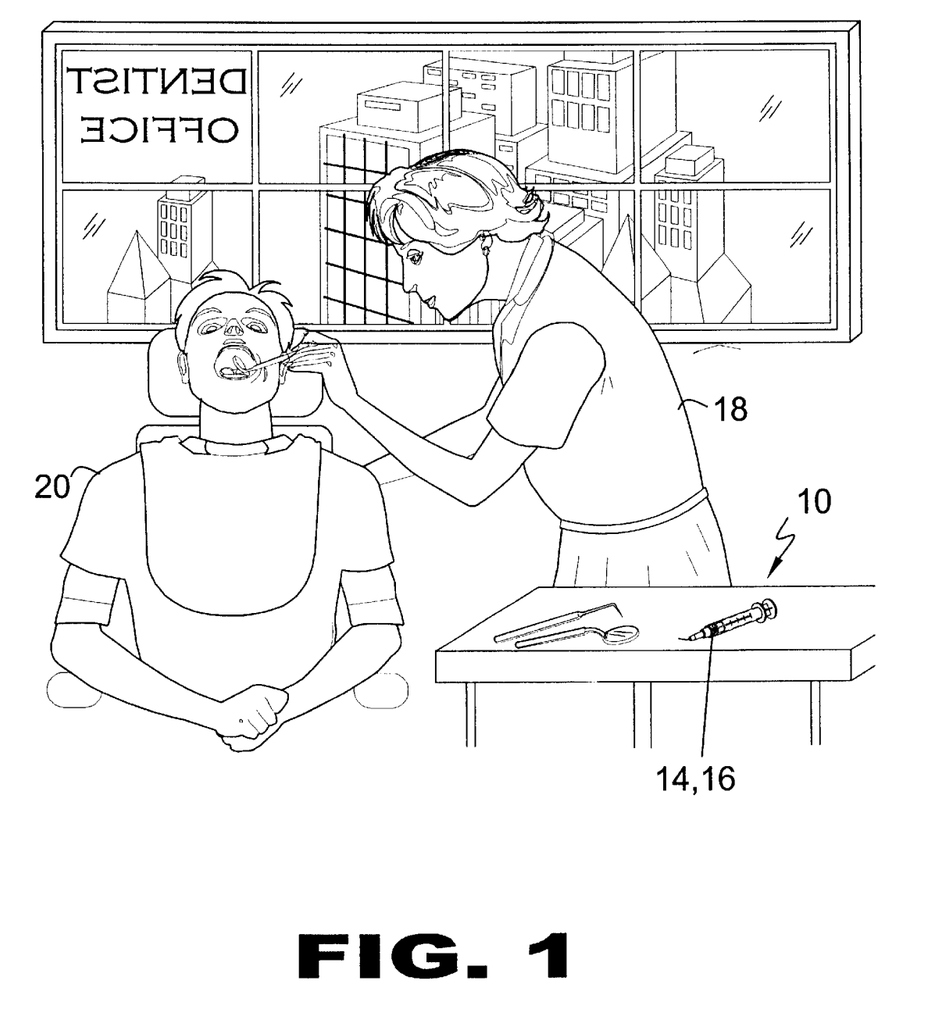
FIG. 1 is an illustrative view of a dentist performing a dental application on a patient.

FIG. 1 is an illustrative view of a dentist (18) performing a dental application on a patient (20). The present invention is a composition and applicator (10) that assists in the cleaning of teeth in dental applications. The composition is an abrasive compound consisting of ground pumice (14) and water soluble lubricant (16).

Figure 2:
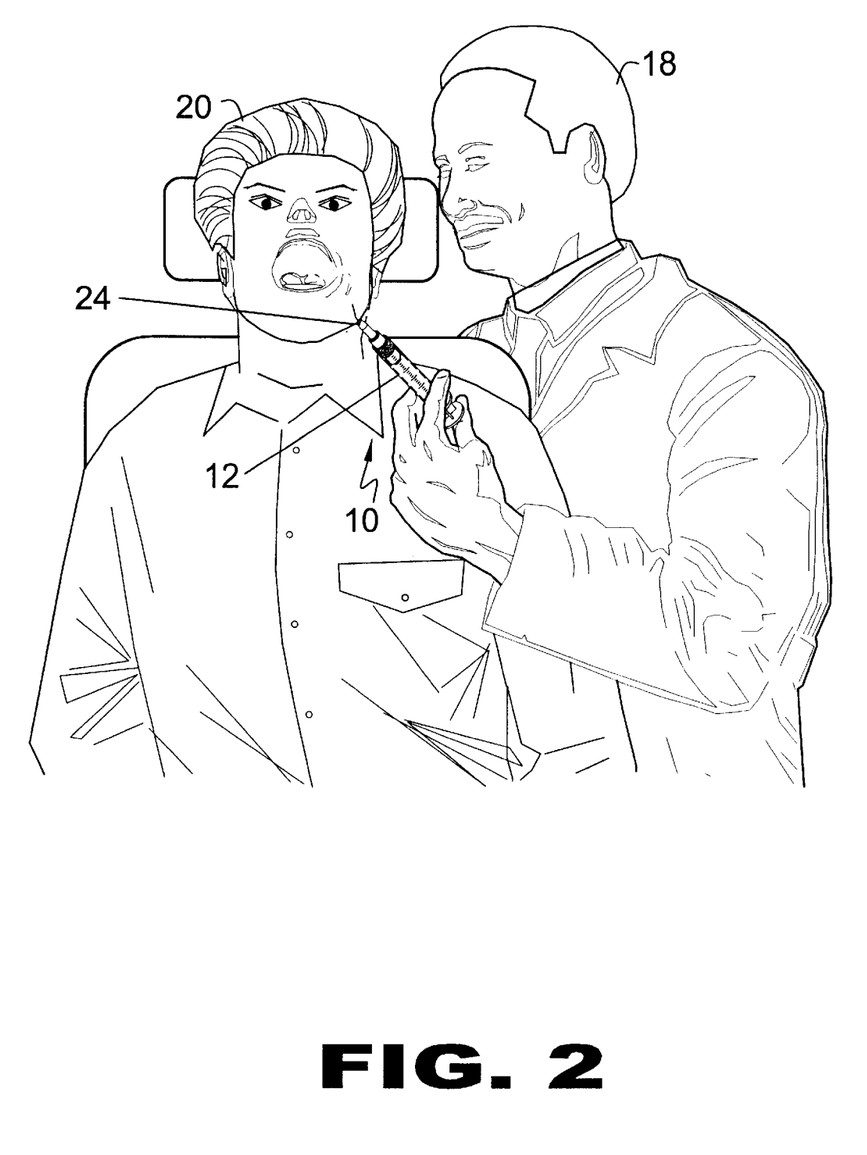
FIG. 2 is an illustrative view of the present invention in use.

FIG. 2 is an illustrative view of the present invention in use. The user (18) of the pumice and water soluble lubricant solution (10) can easily apply the solution to a desired area by using the syringe applicator (12). The prepackaged 20 cc syringe applicator (12) with #20 tip (24), contains a predetermined amount of pumice power and water soluble lubricant solution (10).

Figure 3:
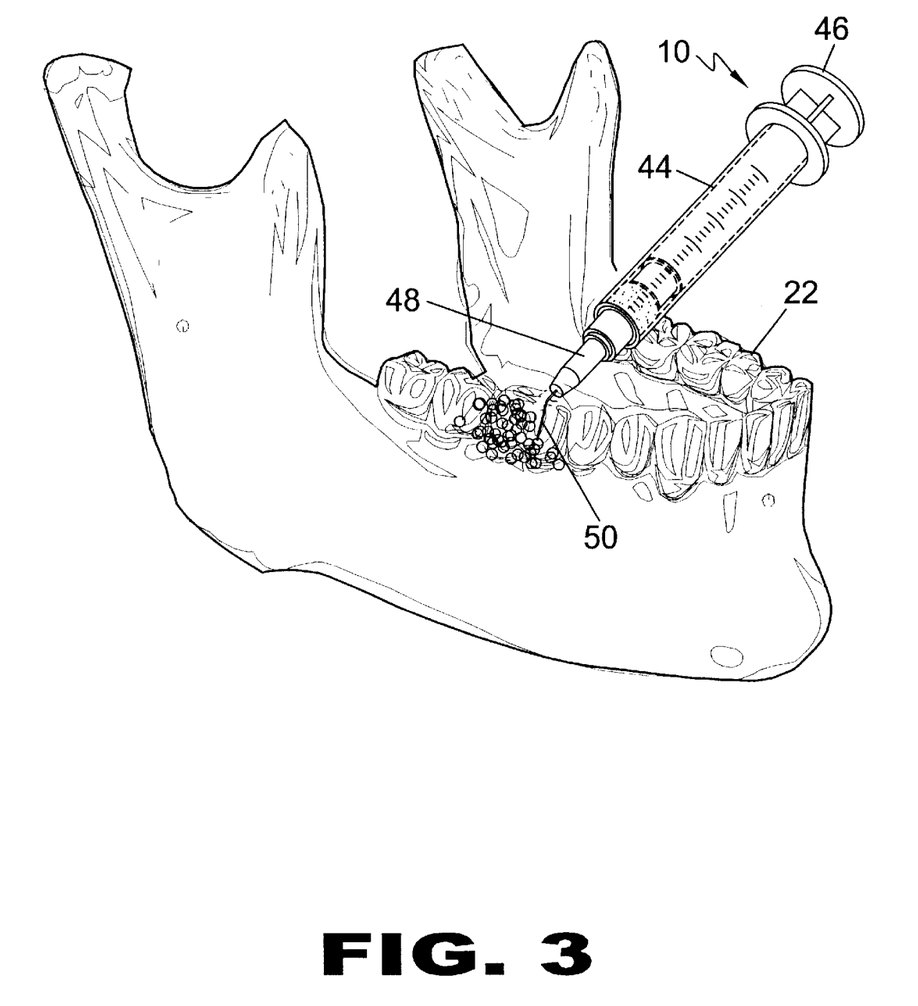
FIG. 3 is a perspective view of the present invention in use.

FIG. 3 is the present invention in use. The present invention, pumice powder with a water-soluble lubricant (10), is applied to the local area of the teeth (22) that is intended to be prepared for dental work. The pumice composition is contained within the canister (44) of the applicator and dispensed by means of a plunger (46). When the plunger (46) is depressed, the pumice composition is dispensed through an egress port (48) and directed with precision to the localized area by means of a needle-like conduit (50).

Figure 4:
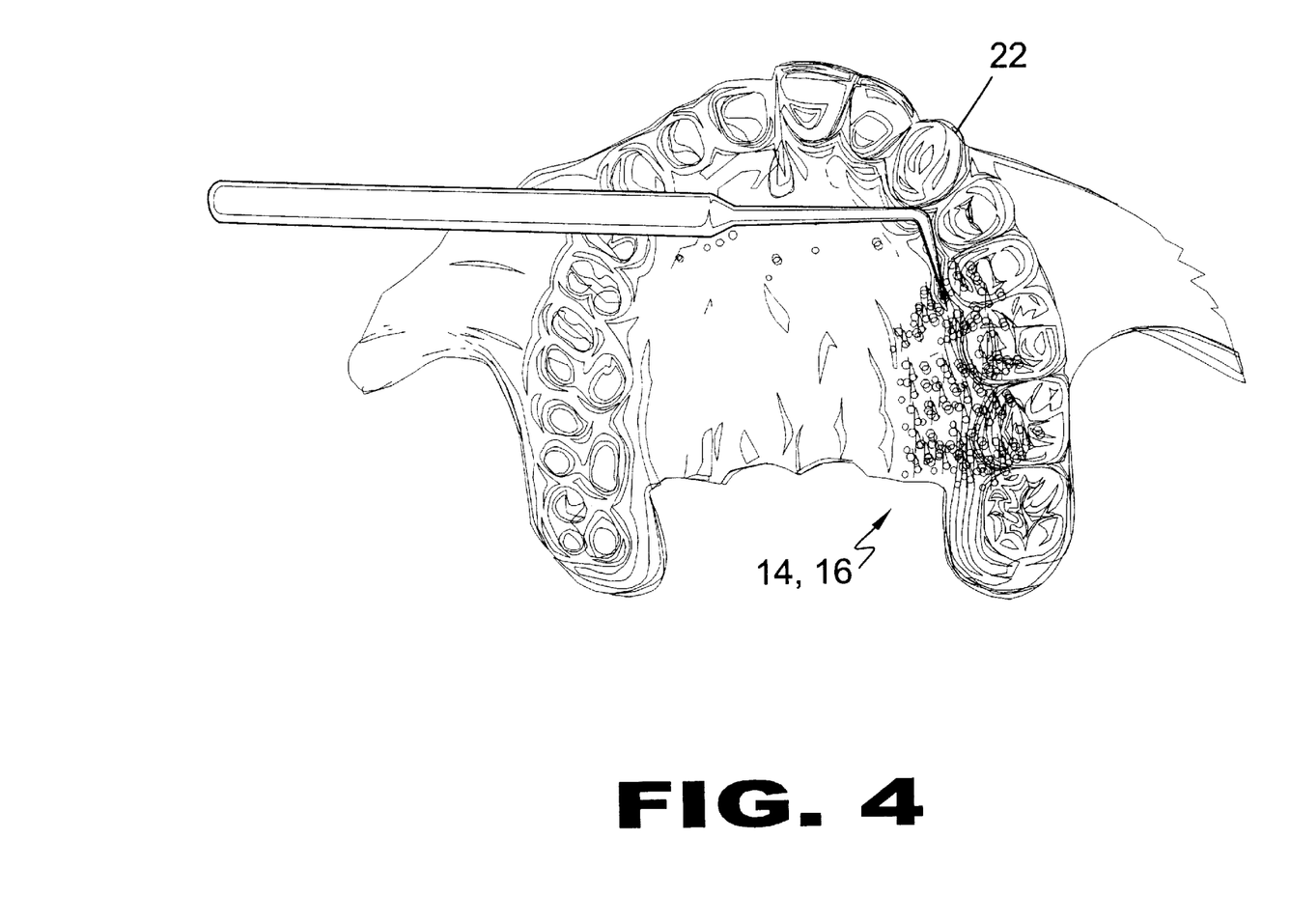
FIG. 4 is a perspective view of the present invention in use.

FIG. 4 is the present invention in use. The present invention overcomes the shortcoming of prior uses of pumice by retaining the pumice powder (14) within a water-soluble lubricant gel (16). In this non-splatter composition, the water-soluble lubricant gel (16) allows the pumice powder (14) to stay in a localized area during teeth (22) cleaning applications.

Figure 5:
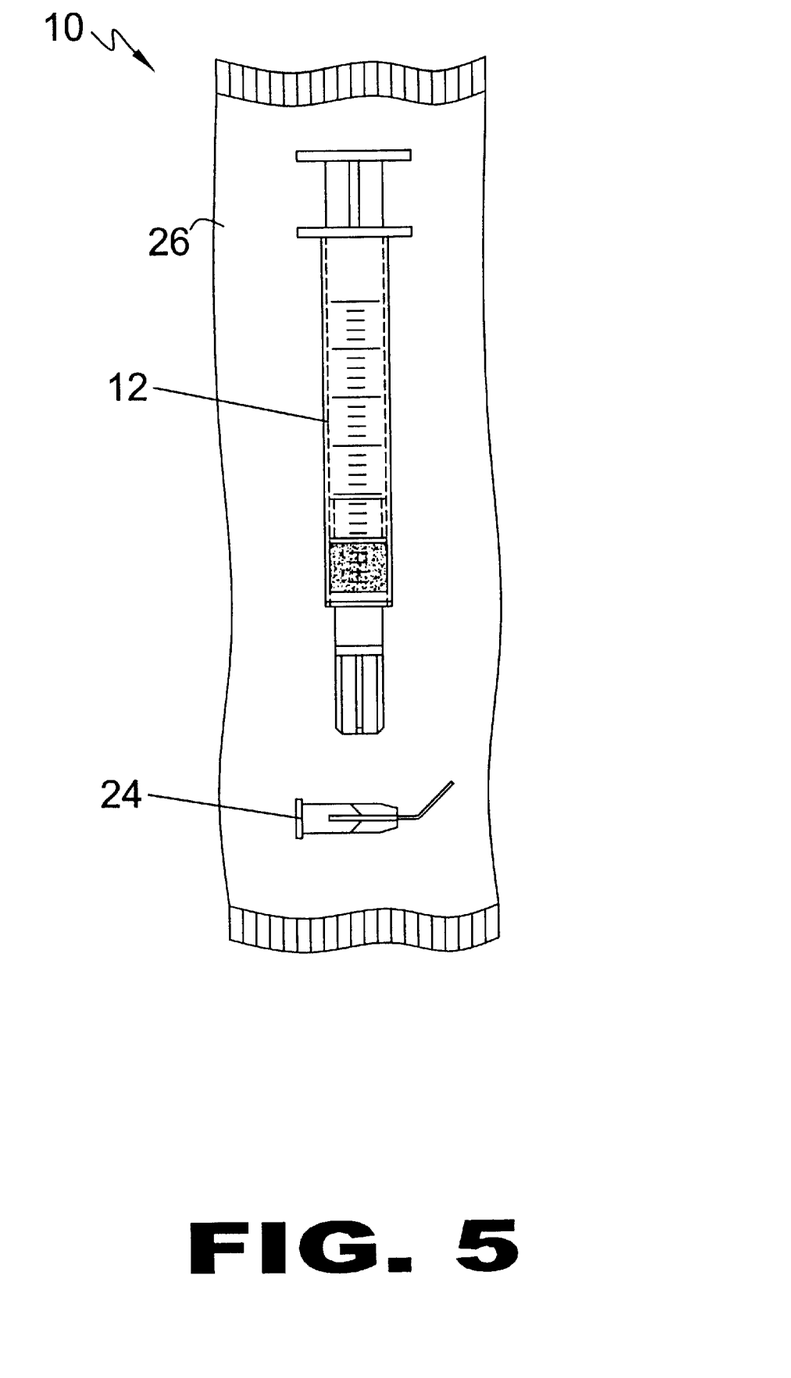
FIG. 5 is the present invention packaged for future use.

FIG. 5 is the present invention packaged for future use. The present invention, pumice powder with a water-soluble lubricant (10), is contained in a package (26) with a premeasured quantity of solution. The solution includes a selected particle size pumice powder (14) measured in microns with an equal part of water-soluble lubricant (16).

Figure 6:
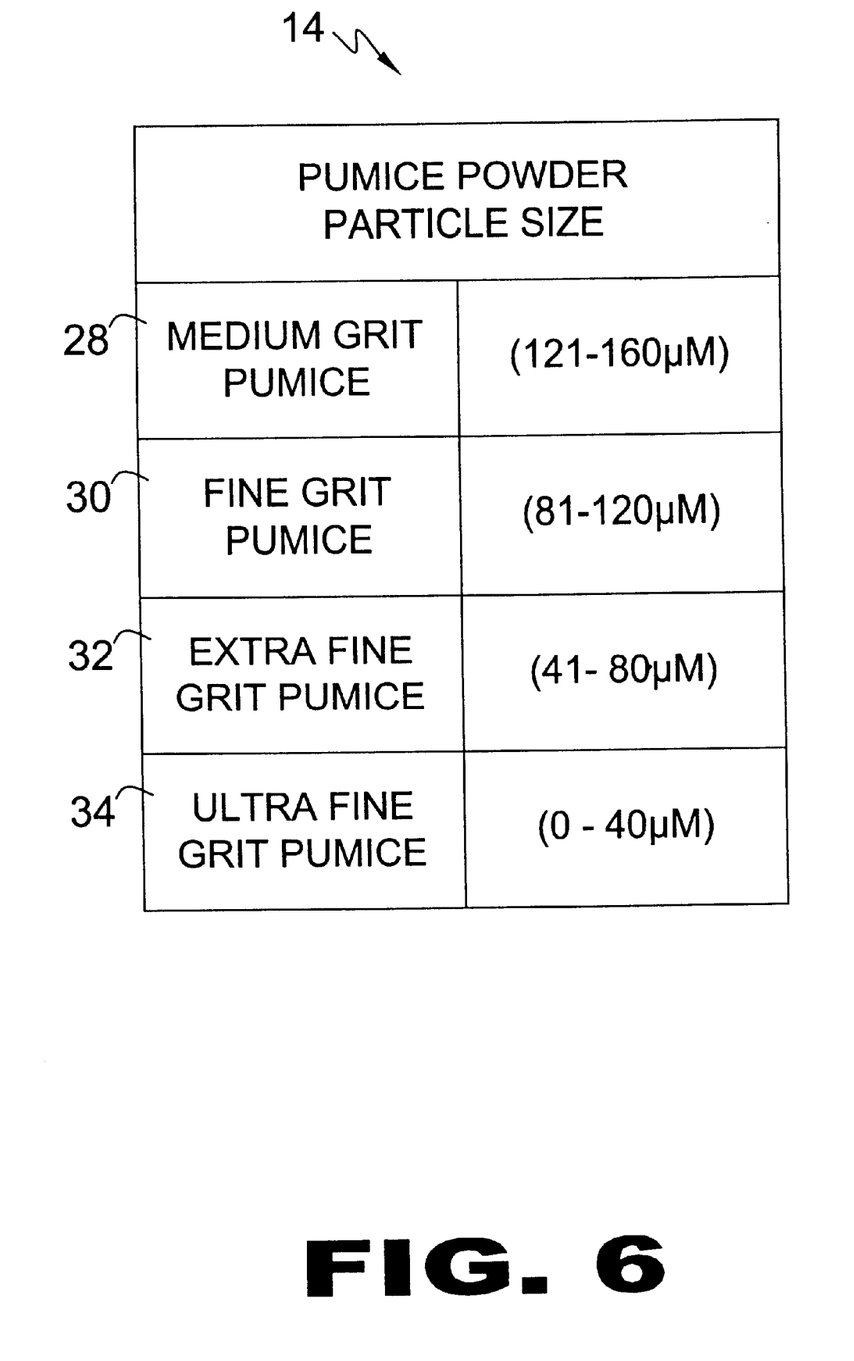
FIG. 6 is a chart of pumice powder particle size variables.

FIG. 6 is a chart of pumice powder (14) particle size variables. Pumice is a light-colored, frothy volcanic rock, usually of dacite or rhyolite composition, formed by the expansion of gas in erupting lava. With its abrasive texture, it is well established that pumice powder (14) is commonly used in dentistry as a cleaning compound. The present invention utilizes micronized pumice powder from 0 to 160 microns. The pumice powder (14) is subdivided into 4 sizes described as; medium (121–160 μm) (28), fine (81–120 μm) (30), extra fine (41–80 μm) (32), and ultra fine (0–40 μm) (34).

Figure 7:
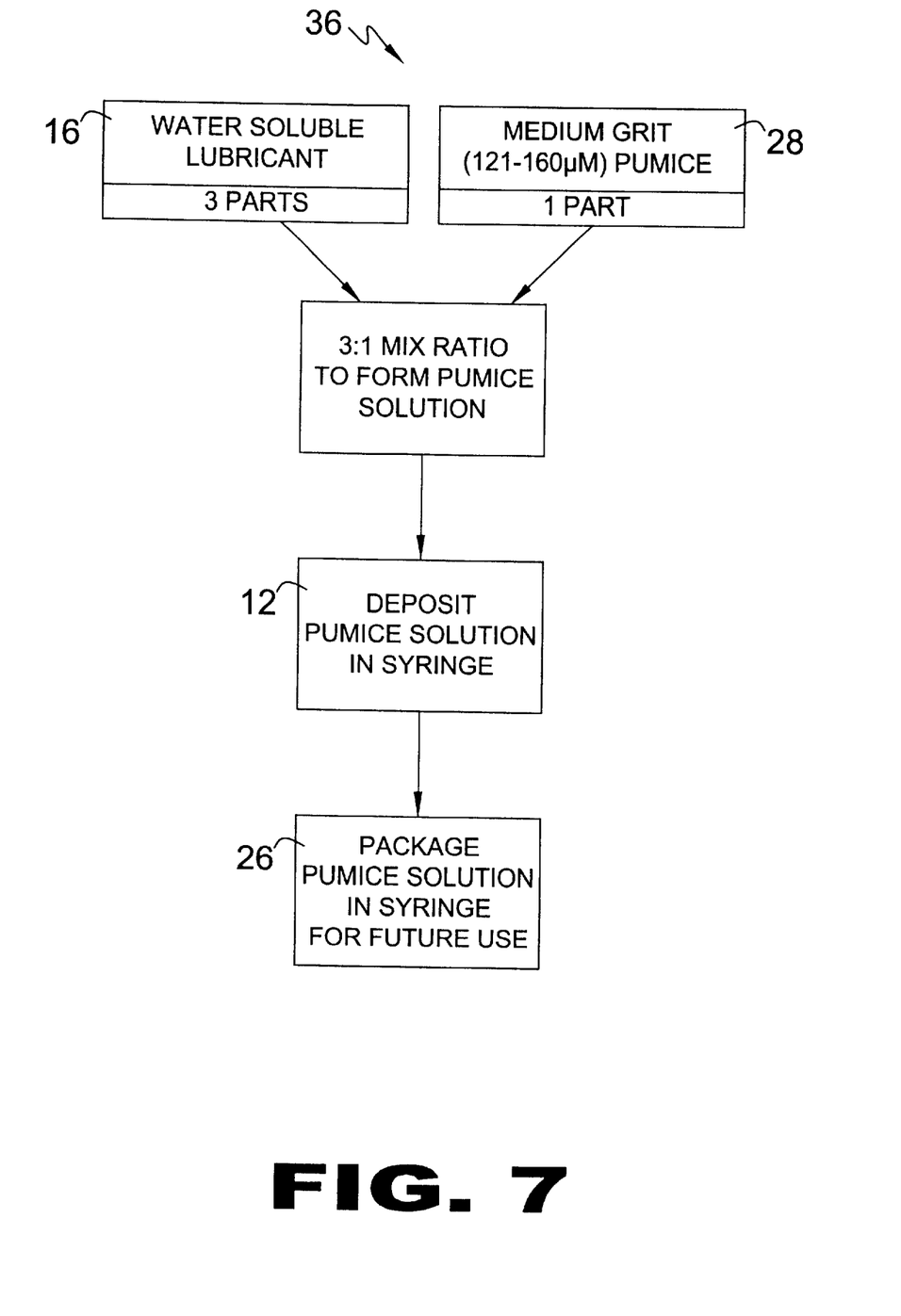
FIG. 7 is a flow chart of the present invention using medium (121–160 $\mu$m) pumice powder.

FIG. 7 is a flow chart of the present invention using medium (121–160 μm) pumice powder (36). The present invention includes an equivalent, 1 part medium (121–160 μm) pumice powder (28) and 3 part water-soluble lubricant (16). The two parts are then mixed into an even consistency pumice solution. The solution is then deposited in a syringe (12) that is used to apply the pumice solution. Finally, the syringe containing the pumice solution is sealed in a package (26) for future use.

Figure 8:
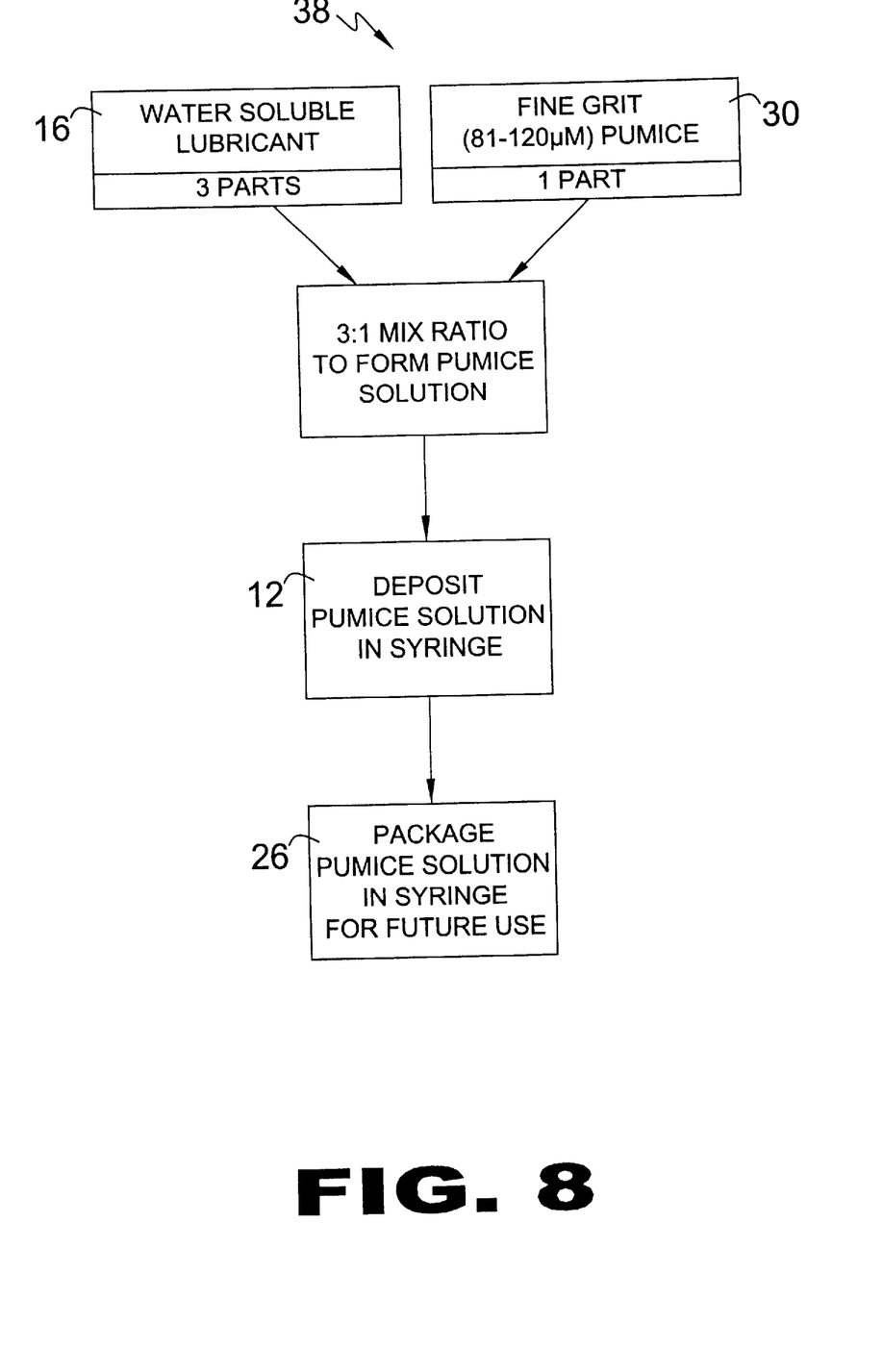
FIG. 8 is a flow chart of the present invention using fine (81–120 $\mu$m) pumice powder.

FIG. 8 is a flow chart of the present invention using fine (81–120 μm) pumice powder (38). The present invention includes an equivalent, 1 part using fine (81–120 μm) pumice powder (30) and 3 part water-soluble lubricant (16). The two parts are then mixed into an even consistency pumice solution. The solution is then deposited in a syringe (12) that is used to apply the pumice solution. Finally, the syringe containing the pumice solution is sealed in a package (26) for future use.

Figure 9:
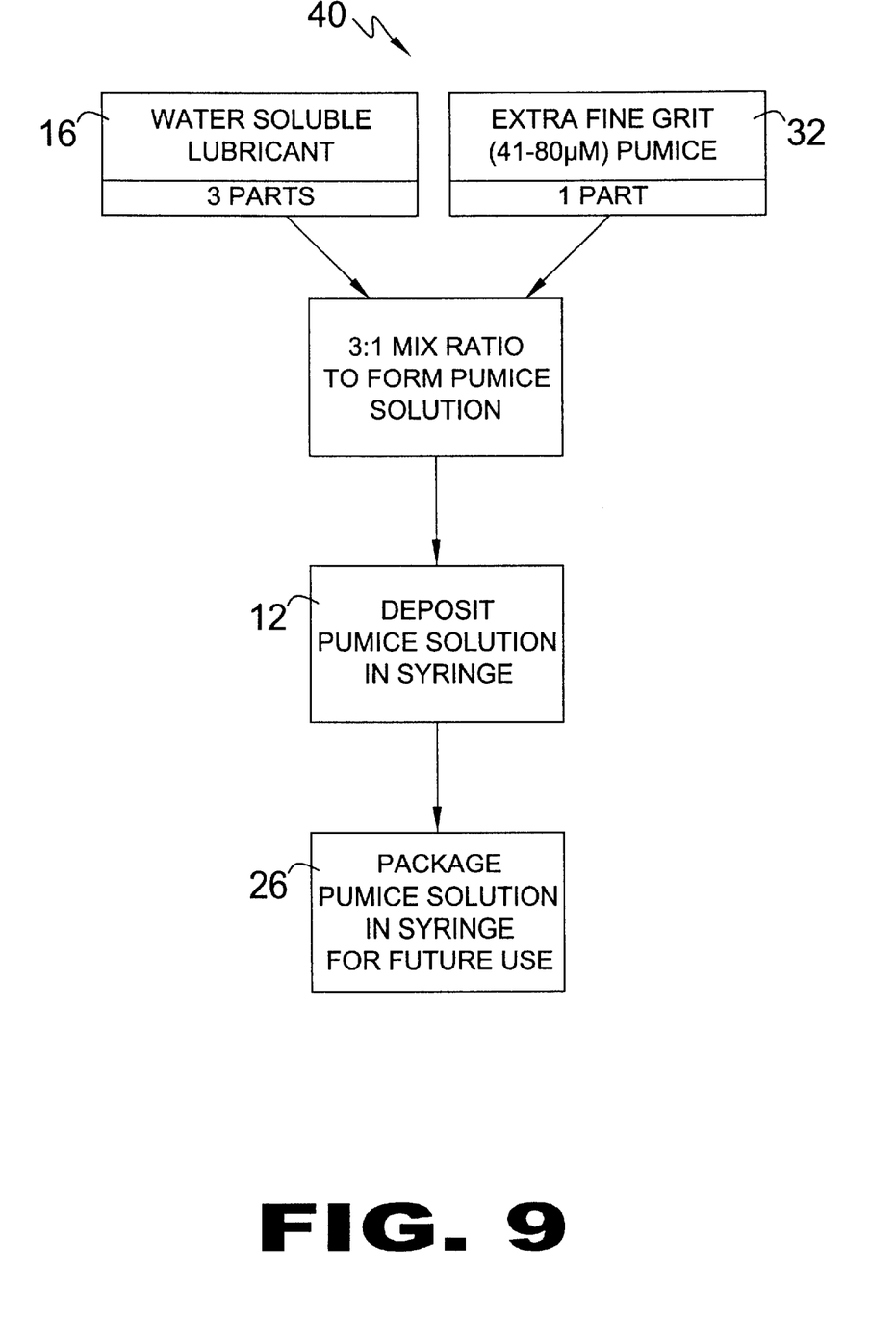
FIG. 9 is a flow chart of the present invention using extra fine (41–80 $\mu$m) pumice powder.

FIG. 9 is a flow chart of the present invention using extra fine (41–80 μm) pumice powder (40). The present invention includes an equivalent, 1 part using extra fine (41–80 μm) pumice powder (32) and 3 part water-soluble lubricant (16). The two parts are then mixed into an even consistency pumice solution. The solution is then deposited in a syringe (12) that is used to apply the pumice solution. Finally, the syringe containing the pumice solution is sealed in a package (26) for future use.

Figure 10:
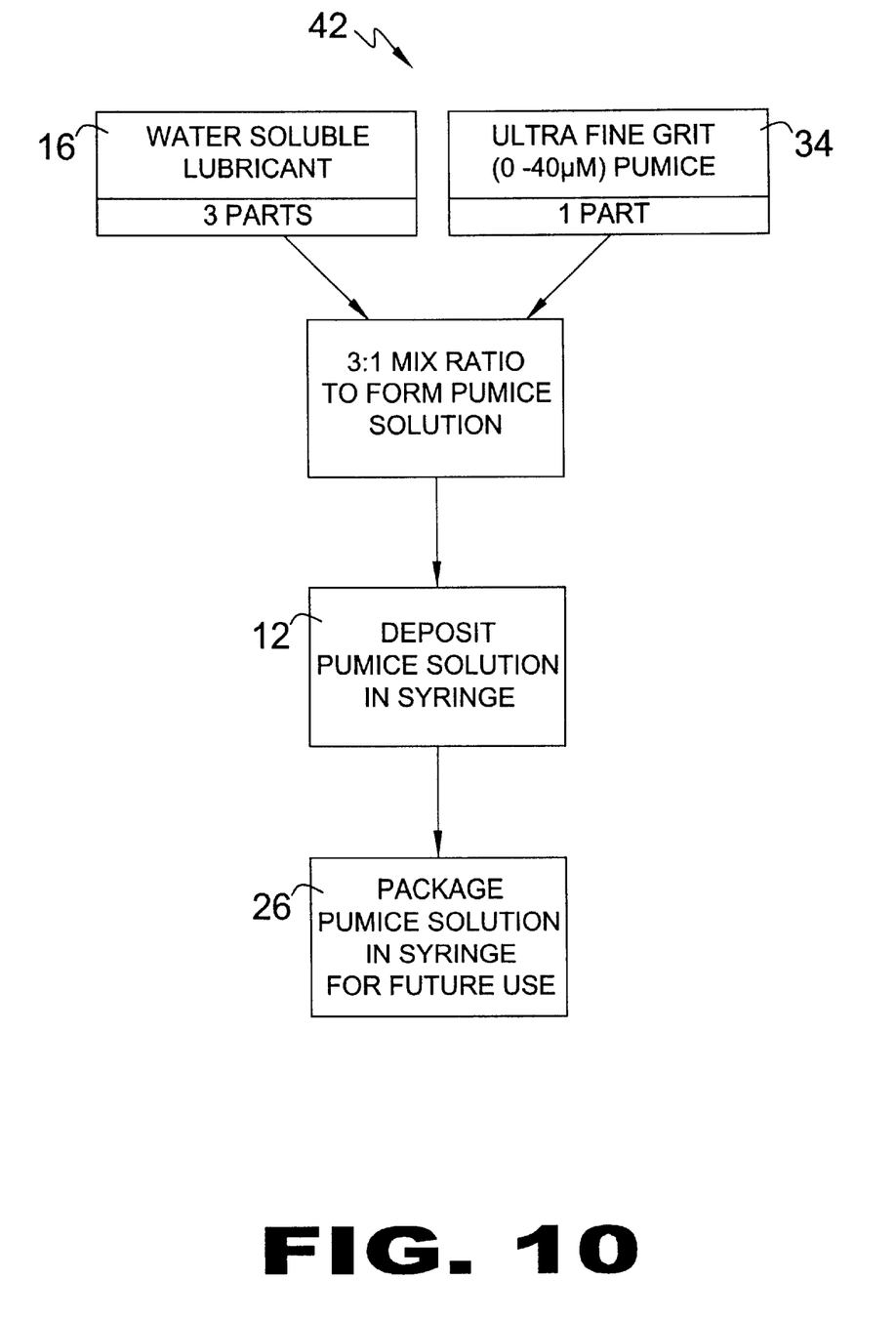
FIG. 10 is a flow chart of the present invention using ultra fine (0–40 $\mu$m) pumice powder.

FIG. 10 is a flow chart of the present invention using ultra fine (0–40 μm) pumice powder (42). The present invention includes an equivalent, 1 part using ultra fine (0–40 μm) pumice powder (34) and 3 part water-soluble lubricant (16). The two parts are then mixed into an even consistency pumice solution. The solution is then deposited in a syringe (12) that is used to apply the pumice solution. Finally, the syringe containing the pumice solution is sealed in a package (26) for future use.

What is claimed is new and desired to be protected by Letters Patent is set forth in the appended claims:

1. The method of dentistry involving dental tooth cleaning with a non-splatter pumice composition containing a prepared water soluble lubricant gel prepared by the process consisting essentially of the steps of mixing three parts water soluble lubricant gel with one part of powdered pumice to form a pumice composition and cleaning the tooth with said composition, said water soluble lubricant gel allowing the pumice powder to stay in a localized area during said tooth cleaning.

2. A non-splattering lubricated dental pumice powder composition consisting essentially of 1 part pumice powder and 3 parts water soluble lubricant gel, said pumice powder consisting of particles selected from the group consisting of 1–40 microns to form an ultra fine grit pumice, 41–80 microns to form an extra fine grit pumice, 81–120 microns to form a fine grit pumice, and 121–160 microns to form a medium grit pumice.

3. The method of claim 1 in which said powdered pumice consists essentially of particles in a specific range selected from the group consisting of 1–40 microns to form an ultra fine grit pumice, 41–80 microns to form an extra fine grit pumice, 81–120 microns to form a fine grit pumice, and 121–160 microns to form a medium grit pumice, and forming an abrasive composition for each pumice particle size so as provide a dentist with a choice of size.

* * * * *